Figure 1:
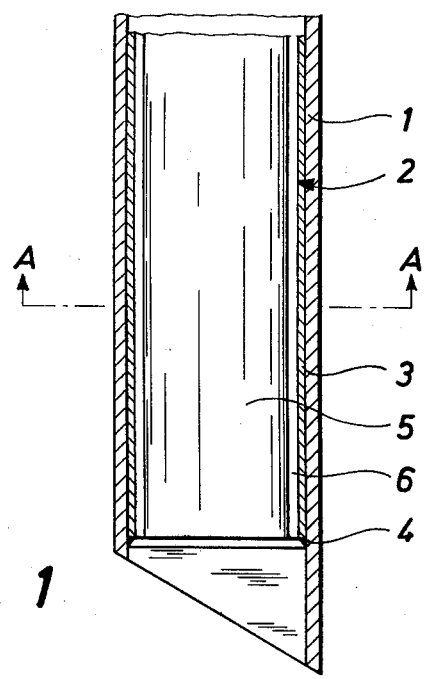

United States Patent [19]

Northeved

[11] 3,961,621
[45] June 8, 1976

[54] SURGICAL TOOL FOR TAKING BIOLOGICAL SAMPLES

[75] Inventor: Allan Northeved, Bagsvaerd, Denmark

[73] Assignee: Akademiet for de tekniske Videnskaber, Svejsecentralen, Glostrup, Denmark

[22] Filed: Jan. 24, 1975

[21] Appl. No.: 543,854

[30] Foreign Application Priority Data

Feb. 6, 1974  Denmark .............................. 654/74

[52] U.S. Cl. ................................. 128/2 B; 128/6; 128/303.1
[51] Int. Cl.² .......................................... A61B 10/00
[58] Field of Search ........................... 128/2 B, 6–9, 128/303.1, 310, 329

[56] References Cited
UNITED STATES PATENTS

| | | | |
|---|---|---|---|
| 3,556,085 | 1/1971 | Takahashi | 128/6 |
| 3,561,432 | 2/1971 | Yamaki | 128/6 |
| 3,685,509 | 8/1972 | Bentall | 128/2 F |
| 3,866,599 | 2/1975 | Johnson | 128/2 L |

FOREIGN PATENTS OR APPLICATIONS 719,538  12/1954  United Kingdom ..................... 128/6

OTHER PUBLICATIONS

Olinger, C. P. et al., *Surg. Neurol*, vol. 2, May, 1974, pp. 151–160, Presented June 11, 1973.

*Primary Examiner*—Kyle L. Howell
*Attorney, Agent, or Firm*—Ladas, Parry, Von Gehr, Goldsmith & Deschamps

[57] ABSTRACT

A surgical instrument for taking biological samples from the interior of a living human or animal body is provided. It comprises a tubular needle with a tubular stiletto snugly and slidably fitted therein, the distal end of said tubular stiletto being sharpened. The stiletto contains optical fiber means for directing light into the interior of the body and for directing reflected light therefrom and is provided with fine air ducts, which, when subjected to a partial vacuum, cause the stiletto to slide forward through the needle into abutment on the interior surface from which a biological sample is to be taken.

2 Claims, 2 Drawing Figures

SURGICAL TOOL FOR TAKING BIOLOGICAL SAMPLES

The present invention relates to a surgical tool for taking biological samples from the interior of a living human or animal body, said surgical tool comprising an elongated needle with a stiletto snugly and slidably fitted therein.

It is known in the art to take a sample of fluid, viz. a sample of the amniotic fluid from a pregnant woman at an early stage of the pregnancy by using a tool of the type stated in the introductory paragraph and by employing ultrasonic exploration, the distal end of the stiletto being provided with a miniature ultrasonic transducer. The fluid sample thus provided is cultured for the purpose of a chromosome analysis to reveal possible undesired defects such as Mongolism. However, the culturing of the amniotic fluid takes three weeks and thus represents a not insignificant portion of the first three months of pregnancy, during which an abortion may be induced without any complications.

However, the culturing of tissue samples may be completed within three days, and it is therefore the object of the invention to provide a surgical tool which makes it possible to take tissue samples from embryos or quite young fetuses.

According to the invention there is provided a surgical instrument for taking biological samples from the interior of a living human or animal body, the instrument comprising an elongated tubular needle with a tubular stiletto snugly and slidably fitted therein, said stiletto tube further comprising means for guiding light from an external light source to an interior surface of said living body, means for guiding light reflected from said interior surface of said body to an external display unit to visualize the picture of said interior surface, and having fine air ducts for applying a partial vacuum to said interior of said body to cause said stiletto to slide forward through the needle into abutment on said interior surface, said stiletto further having a sharpened distal end to cut out a biological sample, which adheres to said distal end of said stiletto by means of the applied partial vacuum.

A preferred embodiment of the instrument according to the invention comprises an elongated tubular needle having a tubular stiletto snugly and slidably fitted therein, said stiletto tube further surrounding a core of lightguiding or optical fibres, said core of optical fibres having a diameter smaller than the inner diameter of said stiletto tube thus leaving a space between the surface of said core and the inner surface of said stiletto tube, which further comprises a number of bundles of optical fibres evenly distributed and spaced apart in said space between the core and the stiletto tube for guiding light from an external light source to an interior surface of said living body, said core guiding light reflected from said interior surface of said body to an external display unit to visualize the picture of said interior surface; said bundles of optical fibres, said surface of said core, and said inner surface of said stiletto defining a number of fine air ducts for applying a partial vacuum to said interior of said body to cause said stiletto to slide forward through the needle into abutment on said interior surface; said stiletto further having a sharpened distal end to cut out a biological sample, which adheres to said distal end of the stiletto by means of the applied partial vacuum.

Thus a surgical tool is provided which will permit of tissue samples being taken from an embryo or fetus without any risk that the embryo or fetus will suffer injury.

Figure 2:
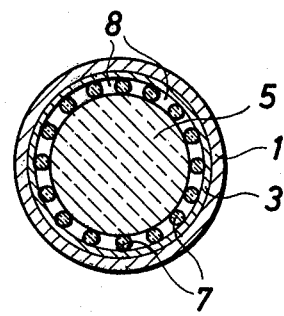

The invention together with further objects and advantages thereof will best be understood by reference to the following specification taken in connection with the accompanying drawing, in which FIG. 1 is a vertical part-sectional elevation of a surgical instrument according to the invention, and FIG. 2 is a cross-section along the line A-A of FIG. 1.

FIG. 1 shows a needle 1 of the type commonly used for taking samples of fluid from the interior of a living organism. A stiletto of a very special design, generally designated by reference numeral 2, is provided inside the needle 1. The stiletto 2 is tubular, and the distal end of the stiletto tube wall 3, as indicated at 4 in FIG. 1, has been given very sharp edge, e.g. by means of electrolytic etching, so that it is possible with said distal end of the stiletto to make a very fine circular cut for instance in a skin surface.

A core 5 of light-conducting fibres (shown in full in FIG. 1) is provided inside the stiletto. The diameter of the core 5 consisting of light-conductors is smaller than the inner diameter of the stiletto tube 3. A number of separate bundles 7 of light-conducting fibres are evenly distributed in the space 6 between the light-conducting core and the stiletto tube wall 3. The spaces 8 between said fibre bundles 7 serve as small air ducts, in which a partial vacuum can be established from outside.

As mentioned in the introduction to the specification it is the object of the invention to provide a surgical tool rendering it possible to take samples from an embryo or fetus at an early stage of the pregnancy without any risk that the embryo or fetus will suffer any injury thereby. According to the invention the tool described above is used in the following way.

When the place and position of the embryo or fetus in the uterus has been detected by means of the known ultrasonic B-scanning method the needle is introduced into the abdominal organs in a direction toward the body part of the embryo or fetus which is most conveniently positioned for the purpose of taking a sample of tissue. This may be for instance a heel. The introduction and the penetration of the needle are monitored partly by means of the ultrasonic apparatus and partly by means of fibre optical equipment being in part built into the stiletto 2.

Light is transmitted through the fibre bundles 7 to illuminate the tissue in front of the needle whereas the light reflected from said tissue is returned through the core 5 of light-conducting fibres, whereafter the picture of the tissue is visualized in any known manner.

When the needle 1 has penetrated the amniotic membrane the distal end of said needle 1 is fixed at a certain short distance from the body part of the embryo or fetus from which a sample of tissue, for instance a sample of skin, is to be taken. Thereafter the stiletto 2 is pushed further forwards through the needle, and when the distal end of the stiletto is only an insignificant distance from the body area in question, this being ascertained by means of the fibre optics, the fine air ducts 8 between the fibre bundles 7 are subjected to a partial vacuum with the result that the stiletto 2 slides forward the remaining small distance and adheres to said area.

The pressure with which the stiletto rests on the body part is readily adjusted by increasing or decreasing the partial vacuum. The stiletto being in its adhering position described above a small circular piece of the skin of the embryo or fetus is cut out by the stiletto tube 3 being turned. The small circular skin sample is lifted free of the body by the stiletto being withdrawn within the needle and by the partial vacuum necessary therefor being provided in the ducts 8. The skin sample is then taken out together with the instrument.

In the account given above the instrument has been used for taking a sample of the skin of an embryo or fetus during the early stage of pregnancy. Certainly, the tool can also be used for taking samples of tissue from other internal organs which it is possible to approach with such an instrument. Thus the instrument also provides the possibility of taking samples of tissue from a considerable number of internal organs without an actual operation being necessary in order to create access to the organ in question.

I claim:

1. A surgical instrument for taking biological samples from an interior surface of living animals including human beings, the instrument comprising an elongate tubular needle with an elongate tubular stiletto snugly and slidably disposed therein, said tubular stiletto having a sharpened annular distal end and having disposed therein means for guiding light from an external light source longitudinally through the stiletto by said sharpened end to said interior surface, means for guiding a reflected image from said interior surface longitudinally back through the stiletto from said sharpened end, and fine air ducts longitudinally extending through the stiletto to said sharpened end for applying a partial vacuum to cause said stiletto, when said sharpened end is adjacant said interior surface, to slide forward through the needle into abutment with said interior surface to cut out a biological sample and to cause said sample to adhere to said distal end of said stiletto.

2. A surgical instrument according to claim 1 wherein said reflected image guiding means is a cylindrical core of optical fibre coaxially disposed with respect to said tubular stiletto and having a diameter smaller than the inner diameter of said tubular stiletto thereby to define an annular space therebetween, said light guiding means is a plurality of bundles of optical fibres evenly spaced apart circumferentially in said annular space, and said fine air ducts are the spaces between said plurality of bundles of optical fibres.

* * * * *